United States Patent
Fischer et al.

(10) Patent No.: US 6,710,183 B2
(45) Date of Patent: Mar. 23, 2004

(54) PROCESS FOR THE SYNTHESIS OF A KNOWN TETRAZOL DERIVATIVE

(75) Inventors: Janos Fischer, Budapest (HU); Ildiko Ballo, Budapest (HU); Endrene Petenyi, Budapest (HU); Janos Kreidl, Budapest (HU); Laszlo Czibula, Budapest (HU); Andras Nemes, Budapest (HU); Ida Deutschne Juhasz, Budapest (HU); Eva Werkne Papp, Budapest (HU); Judit Nagyne Bagdy, Budapest (HU); Istvan Hegedüs, Budapest (HU); Jenöme Farkas, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 0 days.

(21) Appl. No.: 10/182,109

(22) PCT Filed: Apr. 20, 2001

(86) PCT No.: PCT/HU01/00047

§ 371 (c)(1), (2), (4) Date: Jul. 24, 2002

(87) PCT Pub. No.: WO01/81336

PCT Pub. Date: Nov. 1, 2001

(65) Prior Publication Data

US 2003/0078435 A1 Apr. 24, 2003

(30) Foreign Application Priority Data

Apr. 21, 2000 (HU) ............................. 0001618

(51) Int. Cl.$^7$ ......................... C07D 257/00
(52) U.S. Cl. ........................... 548/252
(58) Field of Search ....................... 548/252

(56) References Cited

U.S. PATENT DOCUMENTS 5,206,374 A * 4/1993 Lo ....................... 548/110

FOREIGN PATENT DOCUMENTS

| EP | 0 324 377 | 7/1989 |
|----|-----------|--------|
| WO | WO 93/10106 | 5/1993 |
| WO | WO 95/17396 | 6/1995 |

OTHER PUBLICATIONS

Hungarian Abstract 218,460—Equivalent to U.S. patent No. 5,128,355.

* cited by examiner

Primary Examiner—Joseph K. McKane
Assistant Examiner—Rei Tsang Shiao
(74) Attorney, Agent, or Firm—Herbert Dubno; Jonathan Myers

(57) ABSTRACT

A Process is disclosed for preparing a compound of the Formula (I)

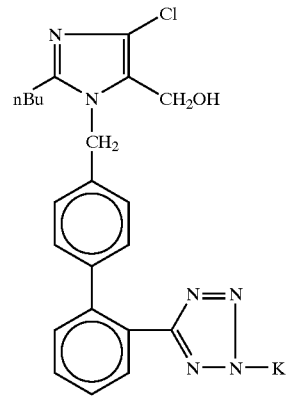

I.

which comprises the steps of:
(a) detritylating a compound of the Formula (III)

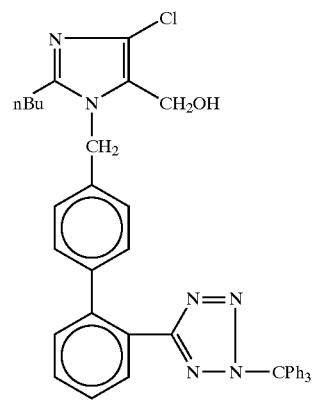

III.

with 0.1 to 1 equivalent of potassium hydroxide in a C1 to C4 straight chain alcohol solvent to obtain a reaction mixture containing the compound of the Formula (I),
(b) changing the C1 to C4 straight chain alcohol solvent in the reaction mixture to an aprotic solvent or a weakly protic solvent, and
(c) following step (b) crystallizing out the compound of the Formula (I) from the reaction mixture.

8 Claims, No Drawings

PROCESS FOR THE SYNTHESIS OF A KNOWN TETRAZOL DERIVATIVE

This application is a 371 PCT/HU01/0097, filed on Apr. 20, 2001. The invention relates to a process for the synthesis of a known tetrazol derivative of formula (I).

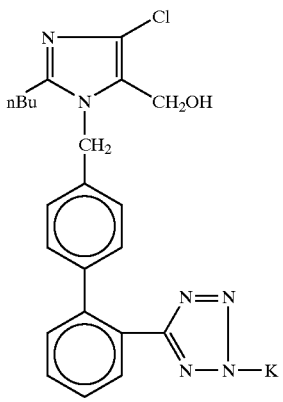

I.

This tetrazol derivative—known as losartan potassium, the chemical name of which is 2-n-butyl-4-chloro-1[(2'-tetrazol-5-yl)-1,1'-biphenyl4-yl)-methyl]-imidazol-5-methanol potassium salt—, is the active ingredient of modern antihypertensive drugs, the angiotensin II receptor antagonists. According to WO 93/10106 and WO 95/17396 PCT Patent Applications, the losartan potassium can be synthesized from a proper acidic compound of formula (II) by reacting it with potassium hydroxide. The compound of formula (II) can be obtained from the triphenylmethyl (or trityl) protected compound of formula (III) by detritylation.

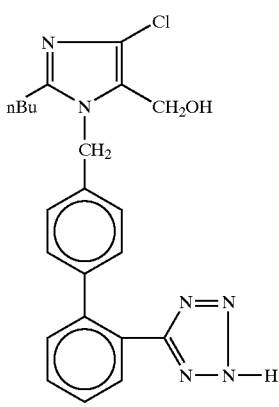

II.

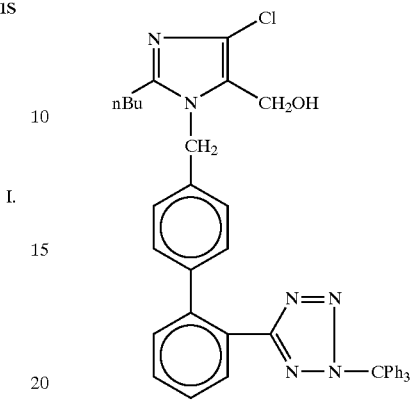

III.

The cleavage of the trityl group was carried out according to the known detritylation procedures—by strong mineral acids (hydrochloric acid or sulfuric acid). The formed trityl alcohol of formula (IV) was removed from the reaction mixture either by filtration or by extraction, the recrystallized and isolated acid was transformed into losartan potassium in aqueous medium with potassium cation (potassium hydroxide or cation-exchange resin), and the latter was crystallized after treatment with organic solvent by removing the water with azeotropic distillation. The solvent of the crystallization was isopropanol or a mixture of cyclohexane and isopropanol.

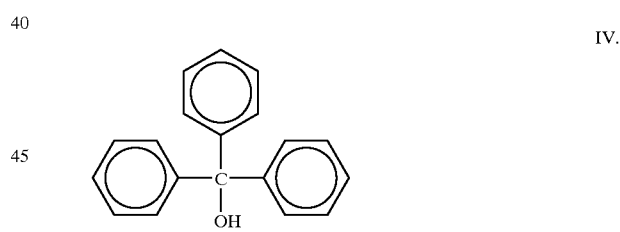

IV.

In the examples of the above patent applications the detritylation was carried out either with aqueous hydrochloric acid or with aqueous sulfuric acid in the presence of tetrahydrofuran or acetonitrile. The total yield of losartan potassium was 72 or 80% from the acidic compound of formula (II), which was isolated after complicated operations. The disadvantages of this process are that the transformation can be carried out only in two steps, the cleavage of the trityl group proceeds by strong, corrosive mineral acid—hydrochloric acid or sulfuric acid—solution and the desired losartan potassium was isolated after addition of aqueous potassium hydroxide with complicated operations: azeotropic distillation, in low yield.

It is known, that during the synthesis of other biphenyltetrazolyl compounds, for example according to U.S. Pat. No. 5,281,603, the trityl protecting group was cleaved by catalytic amount of acid in organic solvents.

According to an other known procedure, for example the one describe in the U.S. Pat. No. 5,281,604, the trityl group of a tetrazolyl-quinazolinone derivative is cleaved by refluxing in a mixture of methanol and tetrahydrofuran for 18 hours. The purified acidic tetrazol derivative was obtained after concentration of the reaction mixture by complicated column chromatography in low yield. From this tetrazol derivative the desired salts can be formed by known procedures.

Summing up, according to the known procedures the losartan potassium of formula (I) was prepared in all cases from the isolated and purified "losartan acid" of formula (II), which was obtained after detritylation by catalytic amount of acid.

The aim of our invention is to elaborate a process, which eliminates the disadvantages of the known multistep procedures and according to which a high quality product can be obtained by simple technology. In our first experiments we found, that if the trityl protected 2-n-butyl-4-chloro-1-[(2'-(2-triphenylmethyl-2H-tetraol-5-yl)-1,1-biphenyl-4-yl)-methyl]-1H-imidazol-5-methanol of formula (III) is treated with equimolar potassium hydroxide in $C_1$–$C_4$ alcohol, then the trityl-alkyl ether of formula (V) containing the alkoxy group of the alcohol and the losartan potassium of formula (I) can be obtained. If the reaction is carried out at reflux temperature for a few hours, the desired product can be obtained practically in quantitative yield.

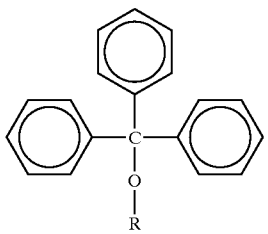

R = $C_1$–$C_4$ straight chain alkyl group

We found surpripingly that this new base catalyzed reaction proceeds very fast and the product can be obtained in high yield. During the detritylation reaction the alcohol reacted as alkoxy anion furnishing the tritylalkyl ether. The ethers of formula (V) have very low solubility in short chain alcohols and therefore can be removed by filtration.

Our other observation was that the reaction took place even if the trityl derivative of formula (III) was treated with 0.1–1 equivalent of potassium hydroxide in a short chain alcohol. In this case the detritylation proceeded in good yield—also with the formation of the trialkyl ether—and the mixture of compounds of formula (I) and (II) was formed. If the reaction mixture was treated with an alcoholic solution containing an equivalent amount of potassium hydroxide calculated on the compound of formula (II), the potassium salt of formula (1) was immediately formed.

According to the above mentioned facts the invention relates to the synthesis of losartan potassium of formula (I), chemical name: 2-n-butyl-4-chloro-1[(2'-(tetrazol-5-yl) -1,1'-biphenyl-4-yl)-methyl]-imidazol-5-methanol potassium, starting from 2-n-butyl-4-chloro-1[(2'-(2-triphenylmethyl -2H-tetrazol-5-yl)-1,1'biphenyl-4-yl)-methyl]1H-imidazol-5-methanol of formula (III), by reacting the compound of formula (III) in an alcohol of formula (VI),—wherein the meaning of R is C, —C4 straight chain alkyl group—with 0.1–1 equivalent of potassium hydroxide and isolating the final product of formula (I) after crystallizing out by changing the solvent to an aprotic or weakly protic solvent.

R—OH

VI

The alcohol used in the process according to the invention is preferably methanol. The reaction is preferably carried out at 20–100° C. more preferably at 50–80° C.

The aprotic dipolar solvent used for the crystallization of the final product is preferably acetonitrile, or straight or branched chain or cyclic aliphatic hydrocarbons can be used as aprotic solvents as well as in an other case sec-butanol can be used as protic solvent.

The reaction can be carried out in any $C_1$–$C_4$ straight chain alcohol, but if the chain is longer the time needed for the detritylation is longer and the yield of the reaction is lower. The most preferred conditions of the reaction are guaranteed if methanol is used. In this case the yield can be even 95% after a few hours reaction time.

If n-butanol is used in the reaction of (III)→(I) at 80% for 15–20 h, the yield can be higher than 80%.

The apolar tritylalkyl ether of formula (V) formed as by-product has low solubility in the alcohol used and therefore can be removed from the reaction mixture mostly by filtration. The very pure losartan potassium can be isolated in high yield from the alcoholic filtrate by changing the solvent. After evaporating the alcohol by distillation, aprotic apolar solvents (for example cyclohexane, heptane), weakly protic secondary alcohols, such as sec-butanol and surprisingly the aprotic dipolar acetonitrile can also be used for crystallization.

The starting material 2-n-butyl-4-chloro-1-[(2'-(2-triphenylmethyl-2H-tetrazol5-yl)-1,1 biphenyl-4-yl)-methyl]-1H-imidazol-5-methanol of formula (III) can be synthesized according to the literature: J. Med. Chem. 1991, 34, 2525–2547 and J. Org. Chem. 1994, 59, 6391–6394.

The advantages of the process according to our invention can be summarized as follows; the trityl alcohol of formula (IV) formed as by-product in the so far known aqueous acidic detritylation reactions is a polar compound, therefore it can be separated from the also polar losartan potassium only with substantial loss of the desired compound. The isolation of compound of formula (II) by tedious operations (extraction, filtration) was necessary in the former procedures to separate from the formed trityl alcohol. According to our process the difficult, tedious azeotropic distillation, which was used after preparation of the potassium salt in aqueous medium, can be avoided.

Further advantage of our process is, that after the base catalyzed detritylation reaction, which proceeds in short chain alcohols—preferably in methanol—in almost quantitative a yield, the about one order solubility difference in a properly chosen aprotic solvent between the formed apolar tritylalkyl ether and the polar losazrtan potassium makes possible the isolation of the pure, insoluble compound of formula (I) in high yield without preparing the compound of formula (II).

The invention is illustrated by the following not limiting Examples:

EXAMPLE I

Synthesis of Losartan Potassium of Formula (I)

Under nitrogen, in a 500 ml flask a mixture of 175 ml of dry methanol, 20 g (0.026 mol) of 2-n-butyl-4-chloro 1-[(2'-(2-triphenylmethyl-2H-tetrazol-5-yl)-1,1'biphenyl-4-yl)-methyl]-1H-imidazol-5-methanol methyl-isobutyl ketone solvate and 1.46 g (0.026 mol) of potassium hydroxide in 25 ml of methanol was warmed to reflux temperature over a period of 30 min. After refluxing for 4 h, the reaction was cooled to room temperature, treated with 0.6 g of charcoal and filtered. The filtrate was concentrated to a volume of 30–35 ml under diminished pressure, and after addition of 85 ml of acetonitrile again to a volume of 30–35 ml. After addition of further 85 ml of acetonitrile the solution is concentrated to a volume of 60–65 ml. The suspension was stirred at 0–(+)2° C. for 2 h, the precipitated crystals were filtered, washed three times with 30 ml of cold acetonitrile and dried at 70° C. to give 11.5 g (94%) of the title compound.

Mp.: 262–264° C.

EXAMPLE 2

Synthesis of Losartan Potassium of Formula (I)

Under nitrogen, in a 500 ml flask a mixture of 180 ml of dry methanol, 20 g (0.026 mol) of 2-n-butyl-4-chloro -1-[(2'-(2-triphenylmethyl-2H-tetrazol-5-yl)-1,1'-biphenyl-4-yl)-methyl]-1H-imidazol-5-methanol methyl-isobutyl ketone solvate and 0.1 g (0.00178 mol) of potassium hydroxide was refluxed for 3 h. The reaction mixture was cooled to room temperature and after adding 1.35 g (0.0241 mol) of potassium hydroxide in 10 ml of methanol it was treated with 0.5 g of charcoal and filtered. The filtrate was concentrated to a volume of 30 ml under diminished pressure, and after addition of 80 ml of acetonitrile again to a volume of 35 ml. After addition of further 85 ml of acetonitrile the suspension was cooled to 0° C., the precipitated crystals were filtered after 1 h stirring, washed twice with 30 ml of cold acetonitrile and dried at 70° C. to give 11.3 g (93.4%) of the title compound.

Mp.: 261–263° 0C.

EXAMPLE 3

Synthesis of Losartan Potassium of Formula (1)

In a 500 ml flask a mixture of 200 ml of dry ethanol, 20 g (0.026 mol) of 2-n-butyl-4-chloro-1-[(2'-(2-triphenylmethyl -2H-tetrazol-5-yl)-1,1'-biphenyl-4-yl)-methyl]1H-imidazol-5-methanol methyl-isobutyl ketone solvate and 1.45 g (0.026 mol) of potassium hydroxide was refluxed for 9 h, treated with 0.5 g of charcoal and filtered. The filtrate was concentrated to a volume of 30 ml under diminished pressure, and after addition of 150 ml of acetonitrile again to a volume: of 60 ml. The suspension was stirred at 0° C. for 1 h, the precipitated crystals were filtered, washed twice with 25 ml of cold acetonitrile and dried at 70° C. to give 10.6 g (88%) of the title compound.

Mp.: 262–264° C.

EXAMPLE 4

Synthesis of Losartan Potassium of Formula (I)

In a 250 ml flask a mixture of 100 ml of n-butanol, 7.64 g (0.01 nol) of 2-nbutyl-4-chloro-1-[(2'-(2-triphenylmethyl-2H-tetrazol-5-yl)-1,1'-biphenyl-4-,yl)-methyl]-1H-imidazol-5-methanol methyl-isobutyl ketone solvate and 0.56 g (0.01)1 mol) of potassium hydroxide was stirred at 80° C. for 20 h, treated with 0.5 g of charcoal and filtered. The filtrate was concentrated to a volume of 10 ml under diminished pressure, and after addition of 100 ml pf acetonitrile again to a volume: of 60 ml. The suspension was stirred at 0° C. for 1 h, the precipitated crystals were filtered washed twice with 25 ml of cold acetonitrile and dried at 70° C. to give 3.78 g (82%) of the title compound.

Mp.: 263–265° C.

EXAMPLE 5

Synthesis of Losartan Potassium of Formula (I)

Under nitrogen, in a 500 ml flask a mixture of 200 ml of dry methanol, 20 g (0.026 mol) of 2-n-butyl-4-chloro 1-[(2'-(2-triphenylmethyl-2H-tetrazol-5-yl)-1,1'biphenyl-4-yl)-methyl]-1H-imidazol-5-methanol methyl-isobutyl ketone solvate and 1.45 g (0.026 mol) of potassium hydroxide was refluxed for 3 h, treated with 0.4 g of charcoal and filtered at room temperature. The filtrate was concentrated to a volume of 30 ml under diminished pressure, and after addition of 160 ml of heptane again to a volume of 130 ml. The suspension was stirred at 0° C. for 2 h, the precipitated crystals were filtered, washed with cold heptane and dried at 70° C. to give 11.3 g (92.5%) of the title compound.

Mp.: 263–265° C.

EXAMPLE 6

Synthesis of Losartan Potassium of Formula (I)

The methanolic filtrate prepared according to Example 5 was concentrated to a volume of 30 ml under diminished pressure, and after addition of 150 ml of hexane again to a volume of 100 ml. The suspension was stirred at 0° C. for 1 h, the precipitated crystals were filtered, washed with cold hexane and dried to give 11.5 g (94.1%) of the title compound.

Mp.: 262–264° C.

What we claim is:

1. A process for preparing a compound of the Formula (I)

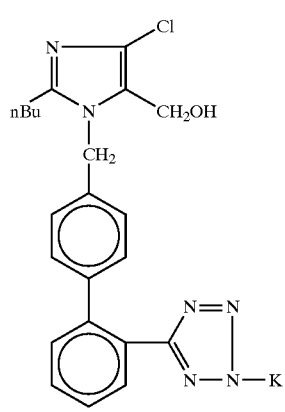

I.

which comprises the steps of:

(a) detritylating a compound of the Formula (III)

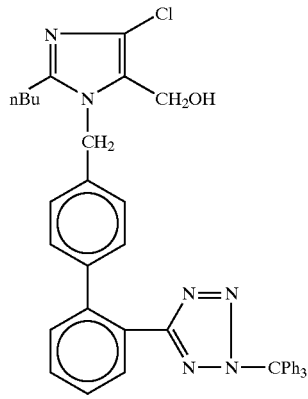

III.

with 0.1 to 1 equivalent of potassium hydroxide in a C1 to C4 straight chain alcohol solvent to obtain a reaction mixture containing the compound of the Formula (I),
(b) changing the C1 to C4 straight chain alcohol solvent in the reaction mixture to an aprotic solvent or a weakly protic solvent; and
C) following step (b) crystallizing out the compound of the Formula (I) from the reaction mixture.

2. The process defined in claim 1 wherein the C1 to C4 straight chain alcohol is methanol.

3. The process defined in claim 1 wherein according to step (a) the detritylation of the compound of the Formula (III) is carried out at a temperature of 50 to 80 degrees centigrade.

4. The process defined in claim 1 wherein according to step (b) the aprotic solvent is acetonitrile.

5. The process defined in claim 1 wherein according to step (b) the aprotic solvent is a straight or branched chain or cyclic aliphatic hydrocarbon.

6. The process defined in claim 1 wherein according to step (b) the weakly protic solvent is sec-butanol.

7. The process defined in claim 1 wherein according to step (a) the reaction mixture further comprise the compound of the Formula (V)

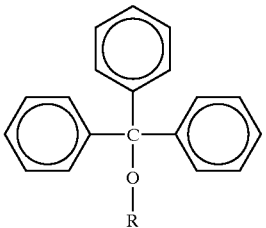

V.

wherein R is a C1 to C4 straight chain alkyl group, as a by-product, and following step (a) the compound of the Formula (V) is separated from the reaction mixture by filtration.

8. The process defined in claim 1 wherein according to step (a) the detritylation is carried out under reflux for a few hours.

* * * * *